(12) United States Patent (10) Patent No.: US 8,496,945 B2
Schlesinger et al. (45) Date of Patent: Jul. 30, 2013

(54) NANOPARTICLE DELIVERY SYSTEMS FOR MEMBRANE-INTEGRATING PEPTIDES

(75) Inventors: Paul Schlesinger, University City, MO (US); Neelesh Soman, St. Louis, MO (US); Gregory Lanza, St. Louis, MO (US); Samuel A. Wickline, St. Louis, MO (US)

(73) Assignee: Washington University, St. Louis, MO (US)

( * ) Notice: Subject to any disclaimer, the term of this patent is extended or adjusted under 35 U.S.C. 154(b) by 0 days.

(21) Appl. No.: 13/109,873

(22) Filed: May 17, 2011

(65) Prior Publication Data

US 2012/0128590 A1 May 24, 2012

Related U.S. Application Data

(63) Continuation of application No. 12/043,063, filed on Mar. 5, 2008, now Pat. No. 7,943,168.

(60) Provisional application No. 60/905,227, filed on Mar. 5, 2007, provisional application No. 60/991,654, filed on Nov. 30, 2007.

(51) Int. Cl.
*A61K 9/00* (2006.01)
*A61K 38/00* (2006.01)

(52) U.S. Cl.
USPC ............. 424/400; 514/1.1; 977/773; 977/915

(58) Field of Classification Search
None
See application file for complete search history.

(56) References Cited

U.S. PATENT DOCUMENTS

| 5,662,932 | A | 9/1997 | Amselem et al. |
|---|---|---|---|
| 6,676,963 | B1 | 1/2004 | Lanza et al. |
| 6,878,376 | B2 | 4/2005 | Spertini |
| 7,186,399 | B2 | 3/2007 | Lanza et al. |
| 7,255,875 | B2 | 8/2007 | Lanza et al. |
| 2005/0119470 | A1 | 6/2005 | Manoharan et al. |
| 2005/0175541 | A1 | 8/2005 | Lanza et al. |

FOREIGN PATENT DOCUMENTS

| JP | 8-511245 | 11/1996 |
|---|---|---|
| JP | 2003-51625 | 5/2003 |
| WO | WO-94/26252 A1 | 11/1994 |
| WO | WO-01/41740 | 6/2001 |
| WO | WO-2007/070827 | 6/2007 |
| WO | WO-2009/151788 | 12/2009 |

OTHER PUBLICATIONS

Rigaud (2002) "Membrane proteins: functional and structural studies using reconstituted proteoliposomes and 2-D crystals", Brazilian Journal of Medical Biological Research, 37(7): 753-66.*
International Search Report and Written Opinion for PCT/US08/55969, mailed Sep. 17, 2008, 9 pages.
Supplementary European Search Report for EP 08731481.1, mailed Jul. 16, 2012, 7 pages.

* cited by examiner

*Primary Examiner* — Robert M Kelly
(74) *Attorney, Agent, or Firm* — Morrison & Foerster LLP

(57) ABSTRACT

Compositions which comprise emulsions of nanoparticles for delivery of membrane-integrating peptides are described. The nanoparticles comprise a liquid hydrophobic core coated with a lipid/surfactant layer which contains the membrane-integrating peptides. Methods to use such compositions are also described.

10 Claims, 9 Drawing Sheets

A

B

C

D

SEQUENCE LISTING

<160> NUMBER OF SEQ ID NOS: 1

<210> SEQ ID NO 1
<211> LENGTH: 26
<212> TYPE: PRT
<213> ORGANISM: Artificial Sequence
<220> FEATURE:

-continued

```
<223> OTHER INFORMATION: Synthetic construct
<220> FEATURE:
<221> NAME/KEY: PEPTIDE
<222> LOCATION: (1)...(26)
<223> OTHER INFORMATION: Melittin

<400> SEQUENCE: 1

Gly Ile Gly Ala Val Leu Lys Val Leu Thr Thr Phe Leu Pro Ala Leu
 1              5                   10                  15

Ile Ser Trp Ile Lys Arg Lys Arg Gln Gln
            20                  25
```

NANOPARTICLE DELIVERY SYSTEMS FOR MEMBRANE-INTEGRATING PEPTIDES

CROSS-REFERENCE TO RELATED APPLICATIONS

This application is a continuation of U.S. Ser. No. 12/043,063 filed 5 Mar. 2008, now U.S. Pat. No. 7,943,168, which claims benefit from U.S. Provisional Application 60/905,227 filed 5 Mar. 2007, and from U.S. Provisional Application 60/991,654 filed 30 Nov. 2007. The contents of these applications are incorporated herein by reference.

TECHNICAL FIELD

Reference to Sequence Listing Submitted Via EFS-Web

The entire content of the following electronic submission of the sequence listing via the USPTO EFS-WEB server, as authorized and set forth in MPEP §1730 II.B.2(a)(C), is incorporated herein by reference in its entirety for all purposes. The sequence listing is identified on the electronically filed text file as follows:

| File Name | Date of Creation | Size (bytes) |
|---|---|---|
| 295002007301Seqlist.txt | Aug. 28, 2012 | 858 bytes |

The invention relates to delivery of membrane-integrating peptides especially those that would otherwise be non-selectively cytotoxic in vivo. More specifically, the invention relates to delivery of such peptides using self-assembling emulsions of nanoparticles wherein a hydrophobic core is coated with a lipid/surfactant layer.

BACKGROUND ART

U.S. Pat. No. 6,676,963 to Lanza, et al., incorporated herein by reference, describes drug delivery in general using targeted "oil-in-water" emulsions, typically emulsions of nanoparticulate fluorocarbon cores coated with lipid/surfactant layers, wherein the lipid/surfactant layer contains a drug to be delivered as well as a targeting agent. As explained in this patent, the prolonged association of the targeted emulsion particles with the surface of a target cell or tissue is distinct from a transient interaction of a non-targeted particle. By binding the particle to the cell surface, the continued circulation of the nanoparticle through the body is halted and the affixed particle is able to interact with the target cell membrane (which is a lipid bilayer) over an extended period of time. This permits effective delivery of the drug contained in the lipid/surfactant layer.

None of the drugs contemplated by Lanza, et al., are membrane-integrating peptides that may undergo endocytosis or that may form pores in the lipid bilayer cellular membrane which can result in cell death due, for example, to non-specific control of substances that enter and exit the cell. These peptides present particular problems and are generally not practical as, for example, antitumor agents, due to their nonspecificity and frequently their overall cytotoxicity in vivo.

Various alternative nanoparticulate compositions containing hydrophobic cores and lipid/surfactant coating are described in U.S. Pat. Nos. 7,255,875 and 7,186,399, both incorporated herein by reference. These patents also refer to earlier compositions used as contrast agents that lack targeting agents.

The problems associated with administering membrane-integrating peptides have been solved by the present invention which resides in the discovery that by associating the membrane-integrating peptides with a lipid/surfactant layer surrounding a hydrophobic core, and optionally targeting the peptide-containing nanoparticle to a tissue for example one whose demise is desired, delivery to this target cell or tissue can be effected so that the peptide can inhibit the growth of the target cells or, indeed, effect cell death while the surrounding tissues and non-target cells are unaffected. The peptide can also facilitate delivery of other therapeutic or diagnostic agents. In addition, the peptide, by virtue of its protected status, is delivered without prior degradation.

DISCLOSURE OF THE INVENTION

The invention is directed to compositions and methods for delivering membrane-integrating peptides by means of self-assembling nanoemulsions. In some embodiments, the nanoemulsions are targeted to specific tissues or cells in animals. These compositions and methods are useful in the treatment of conditions where destruction of specific tissues is desirable, such as for treatment of cancers or unwanted vasculature. In some instances, the cell membrane-integrating effect can be used as an adjunct to other therapies, for example, by opening the blood-brain barrier, increasing vascular endothelial permeability, or by abetting cell entry by therapeutic or diagnostic agents.

Thus, in one aspect, the invention is directed to a composition of nanoparticles containing hydrophobic cores surrounded by a lipid/surfactant layer. The lipid/surfactant layer contains at least one membrane-integrating peptide and, in some embodiments, further contains a targeting agent or ligand specific for an intended tissue or cell target. In some embodiments, the membrane-integrating peptide is also cytotoxic. In some embodiments, the membrane-integrating peptide may further be coupled to an additional therapeutic or diagnostic agent or the lipid/surfactant layer may contain such agents.

In another aspect, the invention is directed to a method to deliver therapeutic or diagnostic agents to tissues or cells selectively using the compositions of the invention. In still another aspect, the invention is directed to effecting cell growth inhibition, necrosis or apoptosis by administering the compositions of the invention in vivo to an animal.

In still another aspect, the invention is directed to a method to prepare the compositions of the invention by admixing the membrane-integrating peptide with preformed nanoparticles in suspension.

BRIEF DESCRIPTION OF THE DRAWINGS

FIGS. 2A and 2B show the association of melittin with liposomes and FIGS. 2C and 2D show melittin associated with nanoparticles. The liposomes are disrupted, but the nanoparticles remain intact.

FIGS. 8A and 8B show binding and internalization of FITC-melittin loaded nanoparticles at 37° C. FIGS. 8C and 8D, respectively, show the effects of ATP depletion and a 4° C. environment on the behavior shown in FIGS. 8A and 8B.

MODES OF CARRYING OUT THE INVENTION

The compositions of the invention comprise nanoparticulate emulsions wherein the nanoparticles contain liquid hydrophobic cores surrounded or coated with a lipid/surfactant layer. The lipid/surfactant layer contains at least one membrane-integrating peptide and may also contain a targeting ligand.

The association of the membrane-integrating peptides useful in the invention with particles makes possible their use as cytotoxins alone or as helper compounds for delivery of other therapeutic or diagnostic agents. Because the membrane-integrating peptide is associated with particulate, it is protected from degradation in the blood. Second, because it is associated with a particulate, the administered emulsion is processed through the liver and spleen where the peptides which are not delivered to the desired location are degraded. Particulate delivery of other drugs does not necessarily have this effect since the liver or spleen may not be able to process them as it does peptides. Third, because of the lipid/surfactant coating, the peptide is delivered directly to the cell membrane. If the nanoparticles further contain a targeting agent, this membrane delivery may be specific to a desired tissue.

The compositions of the invention are, typically, administered intravenously so that the liver/spleen system efficiently detoxifies the peptide that is not provided to the desired location.

The mechanism whereby the peptide is delivered to cells is not completely understood in all cases. Depending on the choice of peptides, the peptide may generate pores in the membrane, or the peptide itself may be introduced into the cell. What is clear is that the peptide integrates with the cell membrane and ultimately enters the cytoplasm.

Figure 1:
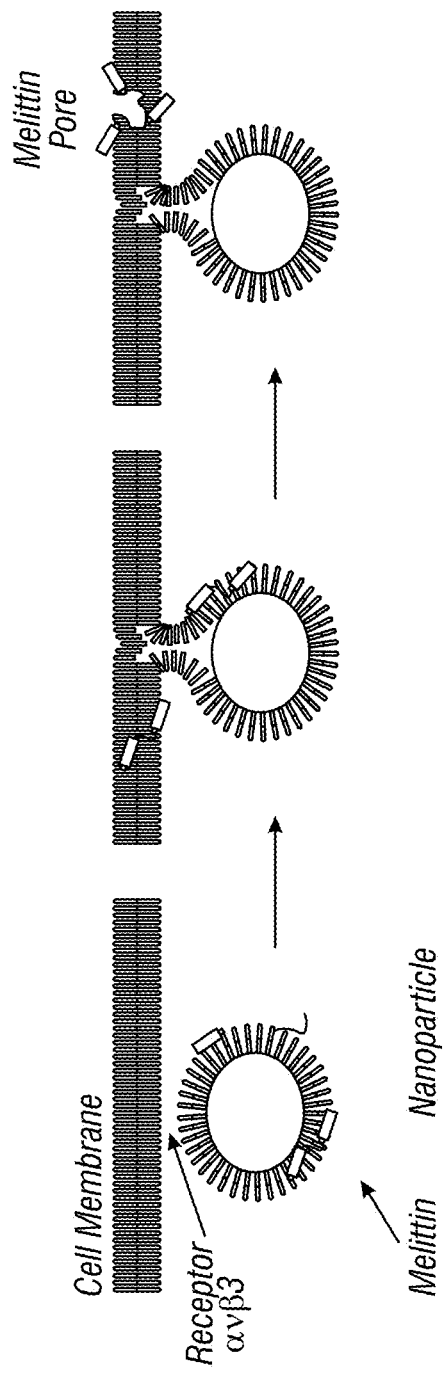
FIG. 1 is a cartoon diagramming one postulated mechanism of delivery of the membrane-integrating peptide to the cell membrane and the formation of pores therein.

FIG. 1 schematically shows one postulated mechanism of transfer of the membrane-integrating peptide from the nanoparticle to the cell membrane or into the cell, as illustrated by melittin, and with a targeted nanoparticle. As shown, the targeting agent binds the nanoparticle to the membrane where it remains for a sufficient time to fuse with the membrane. This permits the peptide to diffuse out of the particle and into the membrane where it can form a pore in the case of melittin, or in the case of other membrane-integrating peptides can be transported into the cell by endocytosis, or by other mechanisms. Melittin forms pores by assembling oligomers in the context of the membrane.

It should be emphasized however, that surprisingly, targeting has been found to be unnecessary.

As noted above, in addition to the advantage of delivery to target cells and tissues, the nanoparticulate compositions stabilize the peptide itself and protect it from degradation in the circulation. Due to the structural features of the nanoparticles contained in the invention emulsions, a stable association of the peptide with the lipid/surfactant layer is achieved, in contrast, for example, to liposomes which are disrupted by association with these peptides.

In short, the invention compositions permit effective use of membrane-integrating peptides in vivo. The subjects of such in vivo treatment are animals in general—i.e., organisms with cells and tissues that are enveloped by a cell membrane and not protected by cell walls. Such subjects include, for example, mammals, including humans, livestock, companion animals, laboratory model systems such as rodents, rabbits, and guinea pigs, avian subjects such as poultry, and fish.

Administration of the compositions is typically parenteral, although in some indications, oral administration may be employed. Other methods include nebulization and introduction to the airway epithelium As used herein, the word "peptide" is not intended to impose an upper limit on the number of amino acids contained. Any peptide/protein which is capable of effecting cell penetration can be used in the methods of the invention. The nature of the lipid/surfactant layer can be adjusted to provide a suitable environment for the peptides/proteins used in the invention depending on the specific characteristics thereof. Thus, the nature of the lipids and surfactants used in this layer are selected so as to accommodate cationic peptides, anionic peptides, neutral peptides, hydrophobic peptides, hydrophilic peptides, amphipathic peptides, etc.

Membrane-integrating peptides useful in the invention include lytic peptides such as melittin and the classic pore forming peptides magainin and alamethicin (Ludtke, S. J., et al., *Biochemistry* (1996) 35:13723-13728; He, K., et al., *Biophys. J.* (1996) 70:2659-2666). Pore forming peptides can also be derived from membrane active proteins, e.g., granulysin, prion proteins (Ramamoorthy, A., et al., *Biochim Biophys Acta* (2006) 1758:154-163; Andersson, A., et al., *Eur. Biophys. J.* (2007) DOI 10.1007/s00249-007-0131-9). Other peptides useful in the invention include naturally occurring membrane active peptides such as the defensins (Hughes, A. L., *Cell Mol Life Sci* (1999) 56:94-103), and synthetic membrane lytic peptides (Gokel, G. W., et al., *Bioorganic & Medicinal Chemistry* (2004) 12:1291-1304). Included as generally synthetic peptides are the D-amino acid analogs of the conventional L forms, especially peptides that have all of the L-amino acids replaced by the D-enantiomers. Peptidomimetics that display cell penetrating properties may be used as well. Thus "cell penetrating peptides" include both natural and synthetic peptides and peptidomimetics.

One particular class of membrane-integrating peptides useful in the invention has the general characteristics of melittin in that it comprises a hydrophobic region of 10-20 amino acids adjacent to a cationic region of 3-6 amino acids. Melittin itself is formed from a longer precursor in bee venom and has the amino acid sequence (SEQ ID NO: 1)
GlyIleGlyAlaValLeuLysValLeuThrThrFlyLeuPro-
AlaLeuIleSerTrpIleLysArgLysArgGlnGln-NH$_2$.

Various analogs of melittin can be identified and tested as described in U.S. Pat. No. 5,645,996, for example. Other designs for peptides useful in the invention will be familiar to those in the art. In the melittin analogs, the hydrophobic region is preferably 15-20 amino acids long, more preferably 19-21 and the cationic sequence is preferably 3-5 or 4 amino acids long.

The toxicity of such peptides is affected by a number of factors, including the charge status, bending modulus, compressibility, and other biophysical properties of the membranes as well as environmental factors such as temperature and pH. The presence or absence of certain moieties (other than the targeted epitope) on the cell surface may also effect toxicity.

In one embodiment, advantage is taken simply of the cytotoxic effects of the membrane-integrating peptides. In treating tumors, for example, it is desirable to effect growth inhibition or cell death specifically on the malignant cells or to exert similar effects on the neovasculature associated with such tumors. Other conditions associated with unwanted neovasculature, such as ocular conditions including age related macular degradation are treatable using the compositions of the invention. Other conditions that can be successfully treated using the compositions of the invention are conditions of the cardiovascular system, and in some cases, conditions of the brain. As stated above, the particulates of the invention protect the peptides from degradation, reduce the toxic effect on bystanders due to processing by the liver, and are helpful in associating the peptide with the cell membrane.

The membrane-integrating peptides of the invention also have an anti-infective role, since they are generally toxic to bacteria, fungi and viruses. These peptides are considered host-defense peptides so that the circulating peptides will have a bactericidal, fungicidal, or antiviral activity.

Illustrated below is the membrane-integrating peptide melittin, which is a water-soluble, cationic, amphipathic 26 amino acid alpha-helical peptide. Suchanek, G., et al., *PNAS* (1978) 75:701-704. It constitutes 40% of the dry weight of the venom of the honey bee *Apis mellifera*. Although a candidate for cancer chemotherapy in the past, melittin has proved impractical because of its non-specific cellular lytic activity and the rapid degradation of the peptide in blood. Attempts have been made to stabilize melittin by using D-amino acid constituents (Papo, N., et al., *Cancer Res*. (2006) 66:5371-5378) and melittin has been demonstrated to enhance nuclear access of non-viral gene delivery vectors (Ogris, M., et al., *J. Biol. Chem*. (2001) 276:47550-47555 and Boeckle, S., et al., *J. Control Release* (2006) 112:240-248). The ultimate effect of melittin is to cause the formation of pores in a cell membrane, and possibly membranes of internal cell organelles, so as to damage the cell and lead to cell death.

In another embodiment a peptide from the Bcl-2-family proteins is employed based on activating or inhibitory activity, for example, BH3 domain peptides (Danial, N. N., et al., *Cell* (2004) 116:205-219). After penetrating to the cellular interior the peptides cause activation or inhibition of the endogenous Bcl-2-family or associated proteins in the cells (Walensky, L. D., et al., *Mol Cell* (2006) 24:199-210). Thus, the cellular machinery of apoptosis can be regulated to a variety of therapeutic goal.

In another embodiment, the lipid/surfactant layer may also contain additional therapeutic agents or diagnostic agents for which cell entry is desired. Thus, the lipid/surfactant layer may also contain small molecule drugs, oligonucleotides such as antisense nucleic acids or gene silencing RNA, nucleic acid vectors, radioisotopes, fluorescent compounds, and the like. These materials may also be attached directly to the membrane-integrating peptide, optionally through a cleavable linkage.

Multiple types of drugs can be included, including drugs which effect positive outcomes, such as angiogenic agents, for example, VEGF, or antiproliferatives, such as paclitaxel. Generally speaking, these delivery mechanisms are employed for any pharmaceutical in the pharmacopeia and more than one type of drug may be delivered, for example, by including a multiplicity of drugs in association with a single particulate delivery system (whether directly with the particles or associated with the membrane-integrating peptide). Alternatively, a composition for administration may be composed of particles bearing different drugs or diagnostic agents targeted to the same tissue, not targeted, or targeted to different tissues with or without combination with non-targeted particles. Compositions of the invention can be mixed and matched in this manner. Alternatively, various compositions either containing single types of particles or mixtures of different types may be administered in sequence.

Other useful drugs for use in the invention are antibacterial, antifungal, or antiviral drugs, including host defense peptides. Because some of these agents are, themselves, peptides, they are particularly convenient for delivery using the systems of the invention.

In one form of this embodiment, one or more compounds or additional peptides to be delivered to a desired target cell or tissue may also be included in the lipid/surfactant layer. As described in the Lanza patent referenced above, nanoparticles, including targeted nanoparticles, are known as vehicles for such administration, but the effectiveness of delivery is further enhanced by including the membrane-integrating peptide of the invention as well. Thus, a multiplicity of drugs or combination of drugs and diagnostic agents may be included in the particle delivered to the cells or tissue. The nature of such therapeutic and diagnostic agents is similar to those described in the succeeding paragraph which discloses an additional mode to carry out the invention. Compositions containing a multiplicity of particles of various types is also included within the scope of the invention. Thus, barriers to entry of the therapeutic or diagnostic compound is enhanced across the cell membrane or even across the blood-brain barrier.

In a second form of this embodiment, the membrane-integrating peptide may itself be coupled to the diagnostic or therapeutic and effect entry of this fused moiety along with itself. For example, additional amino acid sequence of a toxic agent, such as ricin might be fused to the membrane-integrating peptide so as to provide the toxic effect both of the toxin and of the membrane-integrating peptide to the target unwanted cell or tissue. Alternatively, peptide hormones, such as growth hormone, can be targeted to suitable tissue and cell entry effected by the associated membrane-integrating peptide. Therapeutic organic compounds optionally containing labeling radioisotopes may be associated covalently with the membrane-integrating peptides as well. For example, chelating agents which include transition metal or lanthanide ions suitable for magnetic resonance imaging (MRI) can be covalently bound to the peptide.

Suitable therapeutic agents might include, for example, paclitaxel, doxorubicin, daunorubicin, fumagillin, and the like. Other therapeutic drugs include proteins such as growth factors, angiogenic compounds, cytokines and the like. The inclusion of such drugs either fused to the membrane-integrating peptide or also contained in the lipid/surfactant layer may well achieve synergistic effects.

In a third form of this embodiment, the membrane-integrating peptide may be associated with moieties to be delivered into the cell by non-covalent association. For example, DNA or RNA which are negatively charged, can be associated with a positively charged amino acids included in the membrane-integrating peptide. They may also be associated with lipid/surfactant layers that are themselves positively charged. Plasmids, including expression vectors, can thus be transfected into cells by association with the membrane-integrating peptides of the invention.

The nanoparticles contained in the invention compositions comprise hydrophobic cores typically comprised of, or consisting essentially of, fluorochemicals such as perfluorocarbons. Alternative halogenated hydrocarbons can also be used. The lipid/surfactant layer is typically composed of lecithins and other suitable detergents. A detailed description of the construction of such particles is provided in U.S. Pat. Nos. 6,676,963, 7,255,875 and 7,186,399 to Lanza, et al., which have been incorporated herein by reference and these descriptions need not be repeated here. The nanoparticles comprise cores of perfluorocarbons that remain liquid in vivo and the cores are coated with lipid/surfactant.

In some embodiments, the compositions of the invention also contain, in the lipid/surfactant layer, a targeting ligand. The targeting ligand is specific for a target cell or tissue.

As used herein, a ligand "specific" for a target cell or tissue means simply that the ligand binds sufficiently more tightly to the target than to non-targeted cells or tissues to exert its effect substantially only on the target. Typically, this binding is through an epitope exhibited on the surface of the target cell or tissue. Typical targeting agents include antibodies, aptamers, peptidomimetics and the like and are also described in the above mentioned Lanza patent, as are means for coupling such targeting agents to the nanoparticles. Typically such techniques involve coupling the targeting ligand, usually covalently, to a moiety which can be absorbed into the surfactant layer. Thus, the targeting ligand is often covalently coupled to a component of the lipid/surfactant layer.

On the other hand, the membrane-integrating peptide is simply absorbed into the lipid/surfactant layer. In one method of preparation of the invention, the nanoparticulate suspension, optionally containing the targeting agent, is mixed with the appropriate amount of peptide and incubated for a sufficient length of time to effect absorption. This preparation method has the advantage of permitting the nanoparticulate emulsion to be sterilized prior to the addition of peptide, avoiding conditions that would degrade the peptide itself.

In sum, the invention compositions offer, for the first time, the opportunity to effect cell barrier crossing in a selective manner without hemolysis of red blood cells or destruction of tissues whose existence is desirable.

The following examples are offered to illustrate but not to limit the invention.

Preparation A

Preparation of Liposomes

To compare the behavior of traditional liposomes as peptide carriers to the proposed perfluorocarbon nanoparticle vehicles, liposomes (98 mol % egg lecithin, 2 mol % DPPE) were synthesized as described by Saito, M., et al., *Nat. Cell. Biol.* (2000) 2:553-555. Lipids in chloroform were obtained from Avanti Polar Lipid, Inc., and dried to lipid films by placing them under high vacuum for 3 h to remove traces of solvent. Lipids were dissolved in diethyl ether and suspended in an equal volume of buffer (PBS) 10 mM total lipid concentration. The mixture was then sonicated by immersing the flask in an ultrasonic bath (Laboratory Supplies Co, Hicksville, N.Y.) for 20 s to produce a stable emulsion. After removing the organic solvent under reduced pressure, the resulting liposomes were extruded through 200 nm polycarbonate membrane filter and stored at 4° C. temperature.

Example 1

Preparation of Perfluorocarbon Nanoparticles

Perfluorocarbon nanoparticles were synthesized as described by Winter, P. M., et al., *Arterioscler. Thromb. Vasc. Biol.* (2006) 26:2103-2109. Briefly, a lipid surfactant co-mixture of egg lecithin (98 mol %) and dipalmitoyl-phosphatidylethanolamine (DPPE) 2 mol % (Avanti Polar Lipids, Piscataway, N.J.) was dissolved in chloroform, evaporated under reduced pressure, dried in a 50° C. vacuum oven and dispersed into water by sonication. The suspension was combined with either perfluoro-octylbromide (PFOB), or perfluoro-15-crown ether (CE) (Gateway Specialty Chemicals, St. Peters, Mo.), and distilled deionized water and continuously processed at 20,000 lbf/in$^2$ for 4 min with an 5110 Microfluidics emulsifier (Microfluidics, Newton, Mass.). $\alpha_v\beta_3$-integrin targeted nanoparticles were made by incorporating 0.1 mole % peptidomimetic vitronectin antagonist conjugated to polyethylene glycol (PEG)$_{2000}$-phosphatidylethanolamine (Avanti Polar Lipids, Inc.) replacing equimolar quantities of lecithin.

The $\alpha_v\beta_3$-integrin targeting ligand linked to phosphatidyl ethanolamine has the formula:

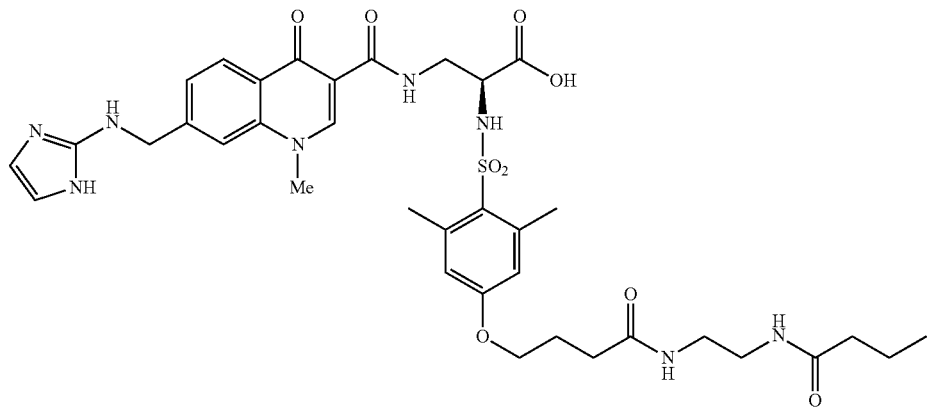

-continued

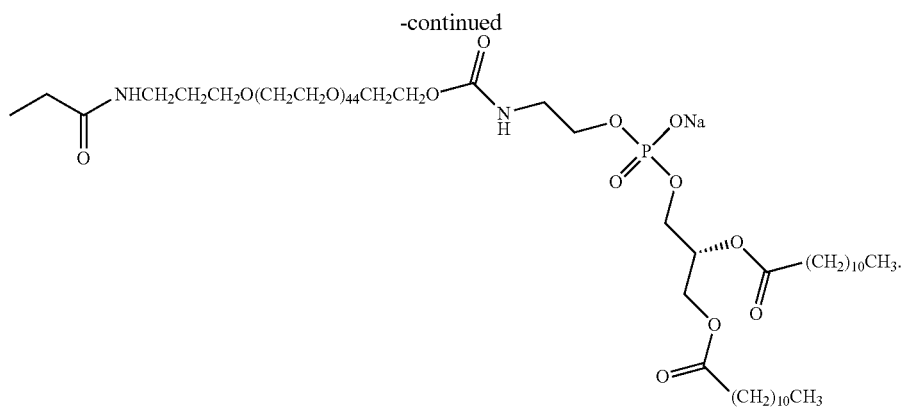

Example 2

Incorporation of Melittin onto Nanoparticles

Melittin-loaded nanoparticles were formulated by mixing known amounts of melittin to perfluorocarbon nanoparticles. Pure melittin peptide material produced by solid-state peptide synthesis was obtained from Dr. Robert Mecham at Washington University Medical School, Department of Cell Biology and Physiology. The melittin was dissolved in 100 mM KCl (pH 7, 10 mM HEPES) at 0.1 mM and 2-20 mL was added to 50 μl of nanoparticle suspension with mixing. After incubation at room temperature for 10 min, the nanoparticles were washed twice by centrifugation (100 g, 10 min) to remove the unbound melittin. The melittin in the supernatant was quantified by measuring the tryptophan fluorescence (described below). Depending on the amount of melittin added, the melittin-loaded nanoparticles yielded molar lipid/melittin ratios ranging from 1,000 to 40.

Example 3

Characterization of Melittin Nano-Emulsions

Size Distribution and Zeta Potential

The size distribution of melittin-loaded nanoparticles was determined by photon correlation spectroscopy (PCS) on a Malvern Zetasizer 3000HS (Malvern Instruments, Malvern, UK). Zeta potential (ζ) values for the nanoparticles were determined with a Brookhaven Instruments PALS Zeta Potential Analyzer (Brookhaven Instruments). Data were acquired in the phase-analysis light scattering (PALS) mode following solution equilibration at 25° C. The Smoluchowski approximation was employed to calculate ζ from the measured nanoparticle electrophoretic mobility (μ):

$$\mu = \in \cdot \zeta \cdot (1.5)/\eta$$

where $\in$ and $\eta$ are the dielectric constant and the absolute viscosity of the medium, respectively.

The melittin-carrying nanoparticles exhibited a mean diameter of 358.8 nm (polydispersity index 0.011) when measured at an angle of 90 degrees using the Malvern Particle Size Analyzer. The zeta potential (ζ) was −31.5 mV. Measurements of ζ were reproducible to within ±1.2 mV of the mean value given by ten determinations of ten data accumulations.

The incorporation of melittin in lipid monolayers of perfluorocarbon nanoparticles was confirmed by surface plasmon resonance studies, fluorescence studies and CD spectroscopy. Each technique allowed independent confirmation of melittin insertion in nanoparticle lipid monolayers. These studies showed that melittin assumes an alpha-helical conformation and dissociates only very slowly from perfluorocarbon nanoparticles.

Electron Microscopy

The effect of melittin on bilayered liposomes and on monolayered perfluorocarbon nanoparticles was examined by transmission electron microscopy. Melittin-loaded perfluorocarbon nanoparticles were generated as described in Example 2. The particles were fixed in 2.5% glutaraldehyde in 0.1 M sodium cacodylate buffer for 30 min on ice. After rinsing the pellet obtained post-centrifugation, the particles were sequentially stained with 1.25% osmium tetroxide, 2% tannic acid, and uranyl acetate following which the pellet was dehydrated and embedded in Polybed 812 (Polysciences, Inc, Warrington, Pa.). The pellet was then thin-sectioned on a Reichert-Jung Ultracut and post stained in uranyl acetate and lead citrate.

For visualizing the liposomes, the electron microscopy mesh copper grids (S160-4) were negatively charged by glow discharge. Liposomes treated with melittin were incubated with the grids for 1 min, after which the grids were gently blotted dry and after washing with distilled water, stained by 2% phosphotungstic acid for 30 s. The liposome and nanoparticle samples were viewed on a Zeiss 902 electron microscope. Recordings were obtained with Kodak E.M. film.

Figure 2A:
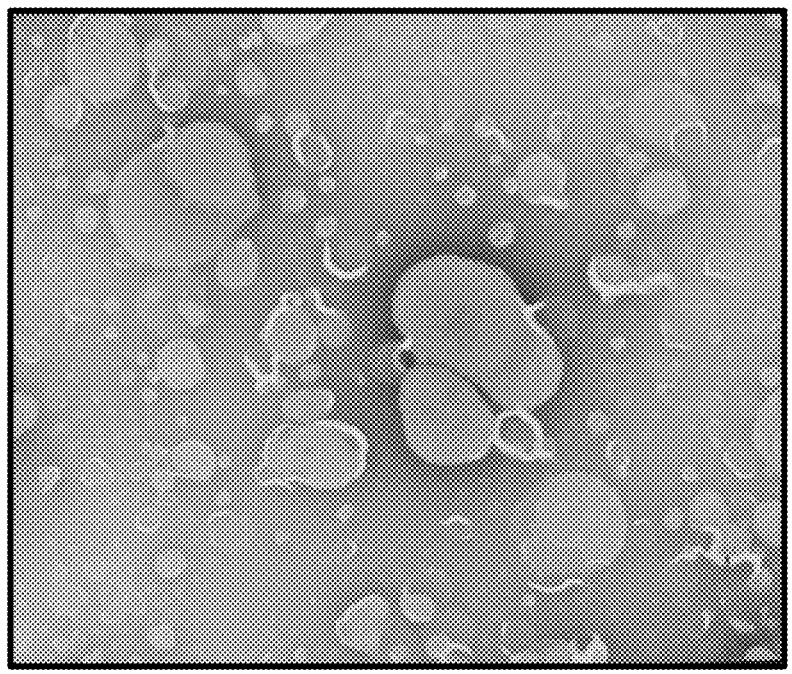
FIG. 2A-2D show transmission electron micrographs of liposomes and of nanoparticles containing melittin.
Figure 2B:
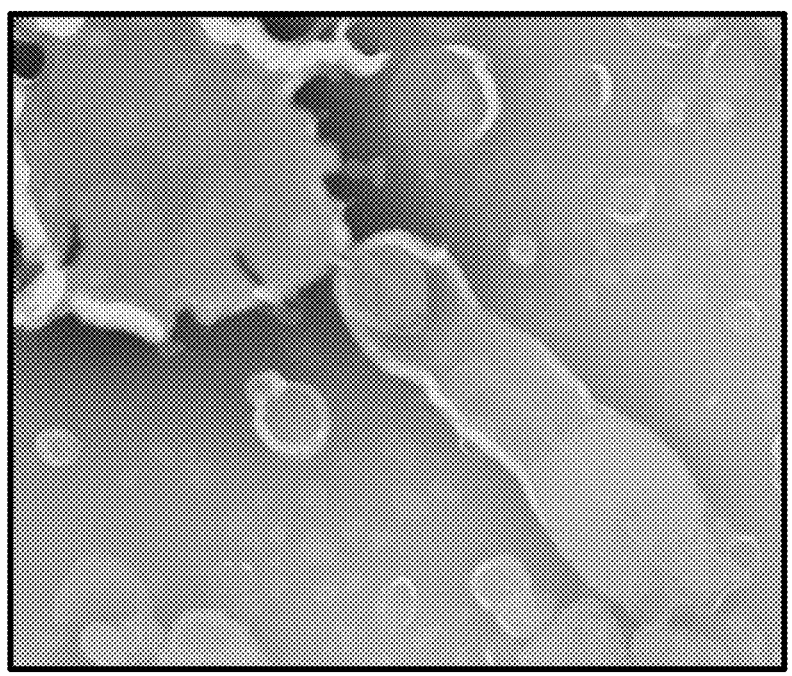
Figure 2C:
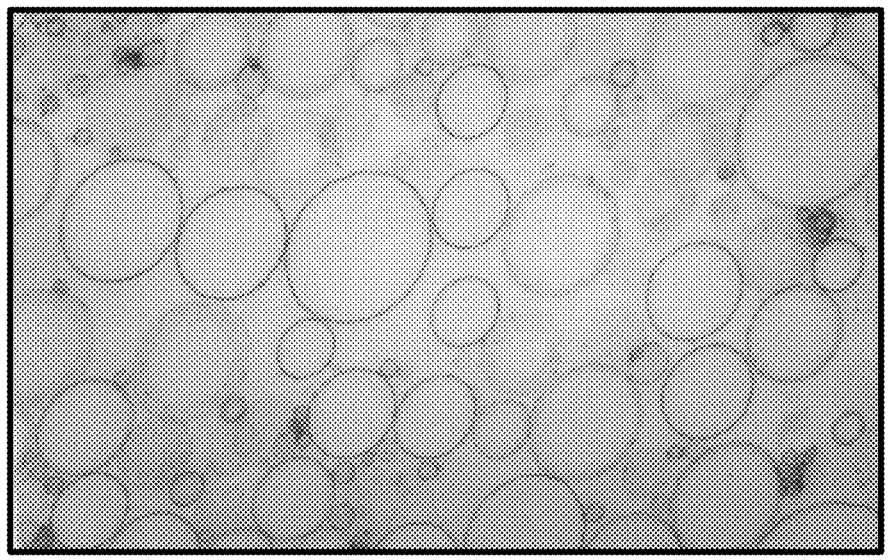
Figure 2D:
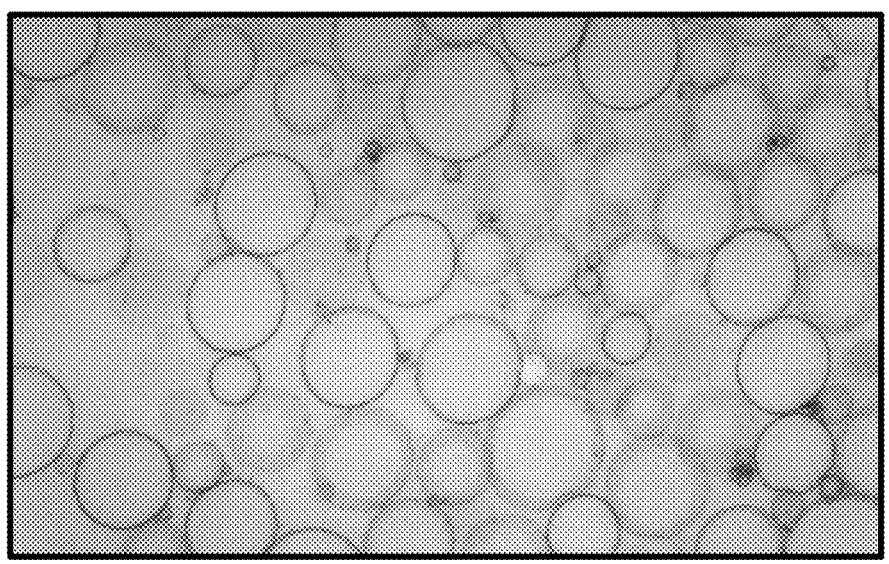

Transmission electron micrographs (TEM's) reveal the structural integrity of melittin-carrying perfluorocarbon nanoparticles as compared with bilayered liposomes that are disrupted after melittin incorporation. The TEM's reveal the typical semilunar membrane blebbing of the disrupted liposomes (FIGS. 2A and 2B), but nanoparticles remain structurally intact (FIGS. 2C and 2D).

As shown in FIG. 2, liposomes (2A and 2B) and perfluorocarbon nanoparticles (2C and 2D) of identical lipid compositions (98 mol % egg lecithin, 2 mol % DPPE) were treated with melittin. The disruptions of lipid membranes leading to loss of liposome integrity and the preservation of structural integrity in nanoparticles due to their unique hydrophobic perfluorocarbon core is evident. Scale bars correspond to 200 nm.

Surface Plasmon Resonance for Kinetic Study

The kinetics of melittin insertion in lipid monolayers of perfluorocarbon nanoparticles was studied by surface plasmon resonance (SPR). SPR detects change in the reflective index of a surface. Biacore-X biosensor and carboxy methylated dextran chip L1 were obtained from Biacore, Inc (Piscataway, N.J.). All solutions were degassed and filtered through a 0.22 μm membrane as recommended. A uniform lipid monolayer on an L1 chip was created by injecting 35 μl PFOB nanoparticles (3 μl/min). Loosely deposited nanoparticles were removed by first increasing the flow rate to 1500 μl/min for 2 min followed by an injection of NaOH (50 μl, 10 mM) to ensure a stable baseline. Complete coverage was confirmed by injecting the negative control bovine serum albumin (25 μl, 0.1 mg/μl in PBS). Melittin in various concentrations was then injected at a flow rate of 30 μl/min (30 μl in PBS; 15 nM to 1000 nM) and the response recorded for 60 minutes. At the end of each experiment the chip was regenerated by two consecutive injections of 3-[(3-cholamidopropyl)dimethylammonio]-1-propanesulfonate (CHAPS) (50 μl, 100 μl/min). A series of sensorgrams was generated for the selected melittin concentrations. The data were analyzed globally by simultaneously fitting the peptide sensorgrams obtained at various concentrations using the BIAevaluation™ software (Biacore, Inc, Piscataway, N.J.). Apparent binding affinity ($K_d$) for melittin interaction with lipid monolayers was estimated by plotting the equilibrium melittin-binding response (Response Units, RU) as a function of injected melittin concentration (μM) and fitting a Langmuir isotherm model.

Figure 3:
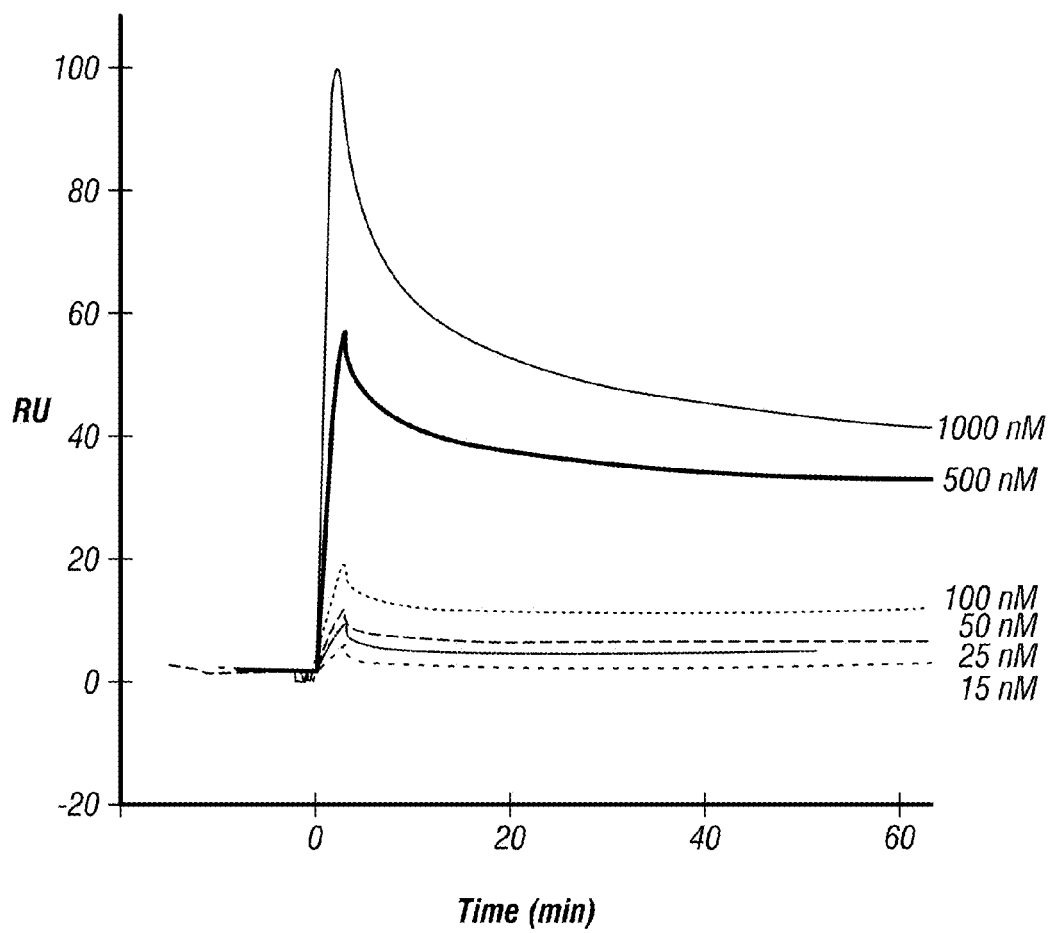
FIG. 3 is a sensorgram showing the kinetics of binding of melittin to lipid monolayers of perfluorocarbon particles coated on a Biacore® L1 Chip.

The results are shown in FIG. 3 which shows the kinetics of binding of melittin to lipid monolayers (lecithin 98 mol %/DPPE 2 mol %) of perfluorocarbon nanoparticles coated on a Biacore L1 chip. Melittin concentrations used were 15, 25, 50, 100, 500 and 1,000 nM. A reproducible maximal response of ~4000 RU was obtained after nanoparticle deposition on an L1 chip. The absence of signal increase after serum albumin injection confirmed the maximal coverage of the L1 chip with nanoparticles. By varying the melittin concentration it was determined that the association rate constant ($k_a$) was $4.5 \pm 0.35 \times 10^6$ $(Ms)^{-1}$, and the dissociation rate constant ($k_b$) was $6.5 \pm 0.41 \times 10^{-3}$ $(s)^{-1}$ providing an equilibrium binding constant $K_a$ $6.3 \pm 1.2 \times 10^8$ M. The high affinity association constant $K_a$ results primarily from the very slow rate of melittin dissociation from perfluorocarbon nanoparticles under these conditions.

Fluorescence Spectroscopy

For fluorescence spectroscopy nanoparticles were prepared at a lipid to melittin ratio of 80. The topology of peptides inserted into lipid bilayers can be studied by measuring their intrinsic tryptophan fluorescence. Melittin contains a tryptophan residue at position 19. Bromine-containing molecules are known to quench the fluorescence of tryptophan either by heavy atom collisional quenching that requires contact between tryptophan and the bromine or Forster energy transfer, because brominated molecules exhibit significant absorption at the wavelength of tryptophan emission. The insertion of melittin in perfluorocarbon nanoparticle lipid monolayer was studied by following the kinetics of tryptophan fluorescence emission (350 nm) after excitation at 280 nm in a fluorescent spectrofluorometer (Varian, Inc, Palo Alto, Calif.) equipped with a mini-sample stirrer. Intensities were corrected for light scatter by subtraction of the signal from a cuvette containing nanoparticles without melittin. Nanoparticles synthesized with a perfluoro-15-crown ether core were used as negative control (no bromine components). The melittin concentration was 10 μM.

The intrinsic tryptophan fluorescence in melittin (excitation 280 nm, emission 350 nm) was used to follow the interaction of melittin with perfluorocarbon nanoparticles. Melittin normally undergoes a "blue shift" (or, a change in emission from 350 nm to 345 nm) upon insertion into lipid bilayers due to the hydrophobic membrane environment. However, no blue shift was manifested when the melittin in solution was incorporated into the lipid monolayer of the nanoparticles.

Figure 4:
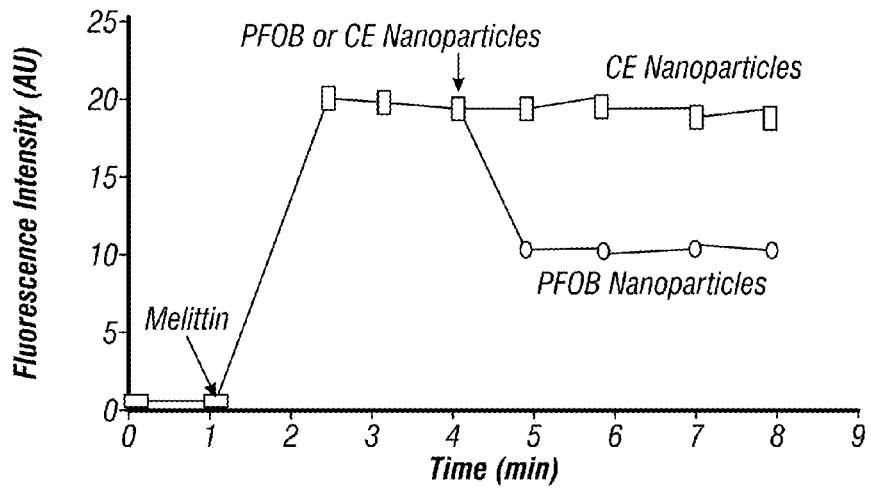
FIG. 4 is a graph showing quenching of the fluorescence emitted by tryptophan contained in melittin when melittin is inserted into the lipid monolayer of nanoparticles.

The intensity of fluorescence of melittin in solution decreased when PFOB nanoparticles were added to the melittin solution. Addition of more PFOB nanoparticles led to a further decrease in melittin fluorescence until a maximum decrease of ~50% was observed after which any further addition of PFOB particles did not cause any change in fluorescence. To confirm that the tryptophan quenching was due to interaction with bromine in the PFOB core, we substituted nanoparticles with a perfluoro-15-crown ether (CE) core. The absence of quenching in the CE nanoparticles confirmed that the tryptophan in melittin was interacting with the bromine in the nanoparticle core of PFOB nanoparticles. These results are shown in FIG. 4.

The mechanism by which brominated hydrocarbons quench tryptophan fluorescence is due either to collision or Forster energy transfer. The Forster distance (the distance at which quenching is 50% efficient is 8 angstroms (Å). Thus the tryptophan residue at position 19 must be located within 8 Å of the brominated core of the nanoparticle or well within the lipid monolayer in the tail region close to the core. This specific interaction could explain in part the nanomolar dissociation rates calculated from surface plasmon resonance experiments. These data confirm the existence of a dynamic equilibrium between the melittin in solution and melittin inserted into the nanoparticle lipid monolayer.

Circular Dichroism Spectroscopy

Circular dichroism (CD) spectroscopy provides information on the secondary structure of peptides and proteins. This method is commonly used in the study of peptides that are incorporated into lipid membranes. The amide chromophore is sensitive to structural changes in the peptide backbone. A Jasco J-810 spectropolarimeter (Jasco, Inc., Eastern, Md.) was used for CD measurements of free melittin and melittin inserted in nanoparticle lipid monolayers. Spectra were scanned in a 1 cm path length quartz cuvette in the far-UV range from 200-260 nm at a scan rate of 50 nm/min and all spectra were collected under argon. Nanobeads and nanobeads with melittin incorporated at a lipid to melittin ratio of 40 were washed by centrifugation and suspended 150 mM NaCl buffered to pH 7 with 5 mM phosphate buffers, at 20° C. with a 4 s response and a band width of 1 nm. An average of 15 scans was used for all spectra which were also corrected for background signal by subtraction of blanks. Data were represented as molar ellipticities [θ]

$$[\theta] = \theta_{obs}/(10 * C * L)$$

where $\theta_{obs}$=observed ellipticity in mdeg, L=path length in cm, and C=melittin concentration in mol/liter.

Figure 5:
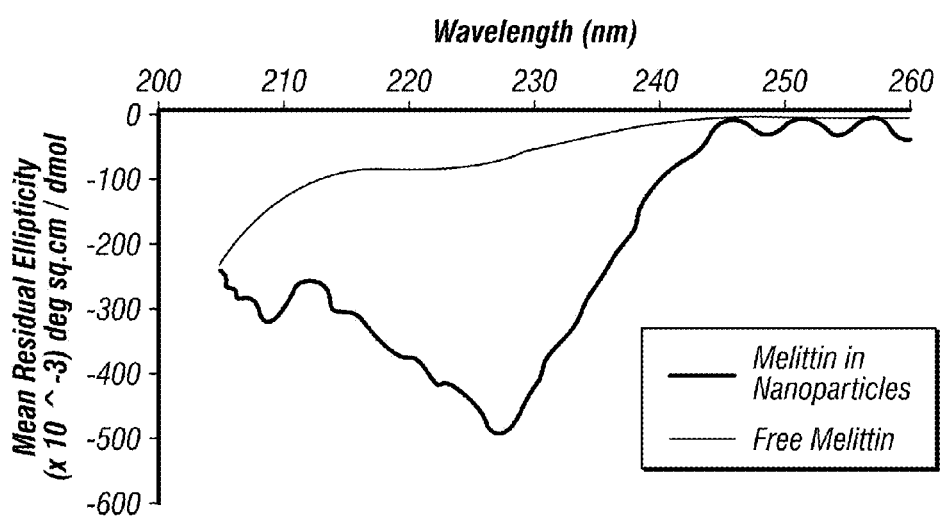
FIG. 5 shows the far-UV CD spectrum of melittin in PBS and in the nanoparticulate lipid monolayers.

Absorption in the region of 240 nm and lower wavelengths is due principally to the peptide bond; a weak but broad n→pi transition centers around 220 nm and a more intense pi→pi transition around 190 nm. When melittin is inserted into the nanoparticle lipid monolayer, a double negative peak is observed: one at 220 nm and other at 208 nm characteristic of an alpha-helical configuration (FIG. 5). Detailed studies of secondary structure should include measuring the ellipticities over a wide range of wavelengths (160-250 nm), but the lower wavelengths were obscured in this case by absorption of buffer or PFOB.

The insertion of melittin into lipid bilayers has been studied previously in the range 205-240 nm and concluded that melittin in the bilayer membrane was primarily alpha-helical.

The results in FIG. 5 indicate that melittin inserted into a lipid monolayer of the nanoparticles assumes an alpha-helical conformation.

Example 4

Interaction of Melittin-Carrying Nanoparticles with Cells

The effect of melittin-loaded nanoparticles on red cells and C-32 melanoma cells was studied by hemolysis assay and the cell proliferation (MTT) assay. Melittin is known to cause red cell lysis and cell death.

Hemolysis Assay

Human umbilical cord blood was obtained from healthy donors after informed consent. The red cells were separated by centrifugation at 200 g for 10 min and resuspended in normal saline. Various concentrations of melittin or melittin-carrying nanoparticles were added to a fixed number of red cells ($5 \times 10^7$ cells) and incubated at 37° C. for 3 hours. The release of hemoglobin was quantified by measuring the absorbance at 540 nm of the supernatant in a Microplate Reader (Model 550, BioRad) after centrifugation. The absorbance of the supernatant obtained by incubating the red cells in water under identical conditions was set to 100%.

Figure 6:
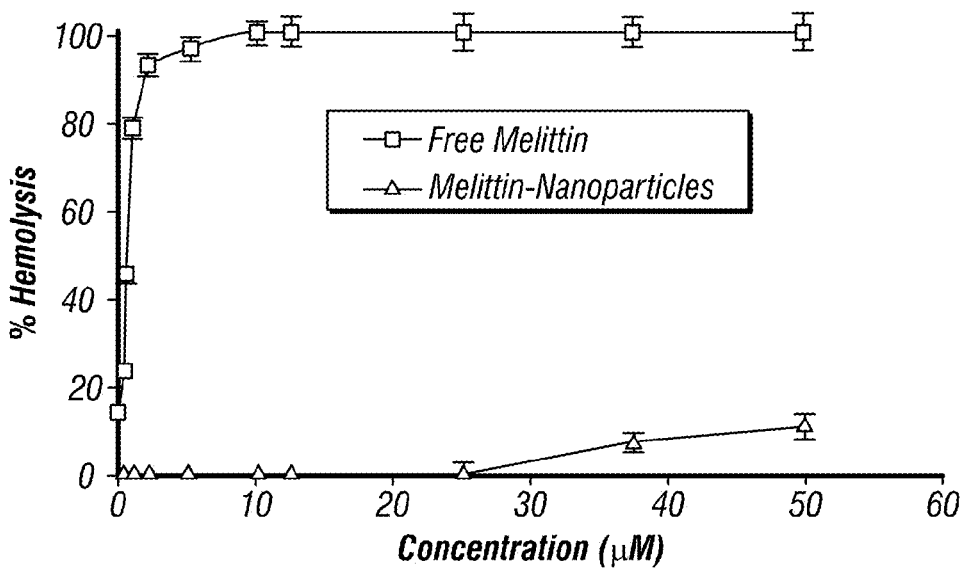
FIG. 6 is a graph showing percent hemolysis effected by free melittin as compared to melittin nanoparticles in a standard hemolysis assay performed on fresh umbilical cord blood.

The $IC_{50}$ (concentration that causes 50% hemolysis) for free melittin is $0.51 \pm 0.12$ µM. The interaction of melittin-loaded nanoparticles with red cells does not cause any significant hemolysis up to a total melittin concentration of 25 µM as shown in FIG. 6. Even up to 50 µM, the melittin-loaded nanoparticles only elicit ~10% hemolysis. These findings show that non-specific interaction of melittin-loaded nanoparticles with red cells would be unlikely to cause significant hemolysis in vivo.

Cell Proliferation Inhibition Assay

The effect of $\alpha_v\beta_3$-targeted melittin-nanoparticles on C-32 cancer cell proliferation was determined by the 3-[4,5-dimethylthiazol-2-yl]2,5-diphenyltetrazolium bromide (MTT) assay. The assay measures the activity of a mitochondrial enzyme that converts MTT, a tetrazolium salt, into a formazan crystal that absorbs at 570 nm.

C-32 melanoma cells were seeded in 96-well plates at a seeding density of 5,000 cells/well. After overnight incubation at 37° C., the cells were treated with free melittin, $\alpha_v\beta_3$-targeted or nontargeted melittin nanoparticles at various concentrations. At the end of 3 hours of incubation at 37° C., the cells were washed three times with PBS and incubated at 37° C. for a period of 72 hours. Then the medium was aspirated, and the cells rinsed with phosphate buffered saline (PBS) and 20 µl MTT solution (Sigma-Aldrich, St. Louis, Mo., final concentration 5 mg/ml in PBS) was added to each well. Cells were further incubated at 37° C. for 30 min, solubilized in 200 µl DMSO to dissolve the precipitated formazan and the absorbance read on a microplate reader (Biorad, Model 550) at 570 nm. Background absorbencies were subtracted and untreated control cells were set at 100% viability.

Figure 7:
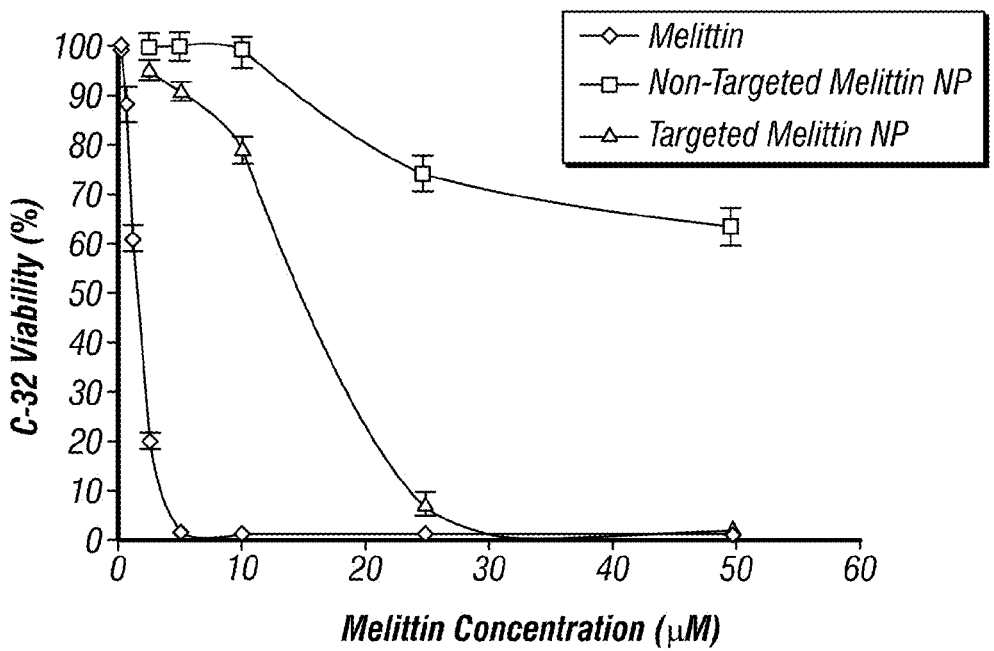
FIG. 7 is a graph showing the viability of C-32 melanoma cells when administered free melittin, non-targeted melittin nanoparticles or targeted melittin nanoparticles.

The effects of melittin on cell proliferation (MTT assay) reveals a dramatic protection when melittin incorporated on the nanoparticles as shown in FIG. 7. Free melittin is highly toxic to C-32 melanoma cells ($IC_{50}$ $0.93 \pm 0.08$ µM). When incorporated into nontargeted nanoparticles, there is an 80-fold increase in $IC_{50}$ (~80 µM), indicating protection from the effects of melittin. However, when melittin-containing nanoparticles are targeted to cells that over-express the integrin $\alpha_v\beta_3$, the $IC_{50}$ falls to $15.2 \pm 0.08$ µM. Thus, the incorporation of melittin in $\alpha_v\beta_3$-integrin targeted perfluorocarbon nanoparticles significantly attenuates its non-specific toxic effects on normal cells, but targeting permits toxic effects to be exhibited on target cells.

Mode of Cell Death

To determine whether cell death caused by melittin occurred by apoptosis or necrosis, the binding of Annexin-V FITC to phosphatidylserine was measured by flow cytometry. One of the early events in apoptosis involves translocation of phosphatidylserine to the outer cell membrane, exposing annexin binding sites. Membrane integrity is preserved until the late stages of apoptosis, but is compromised very early in necrosis. Flow cytometry analysis of annexin-V FITC binding and 7-AAD staining illustrates that the dominant mechanism of cell death from melittin-loaded perfluorocarbon nanoparticles involves apoptosis.

Annexin-V FITC (Sigma, St. Louis, Mo.) and 7-amino-actinomyosin D staining solution (7-AAD, Becton Dickenson Biosciences, San Jose, Calif.) were used to stain the phosphatidylserine in the outer cell membrane and nucleic acids, respectively.

Cells were harvested after 1 hour of incubation at 37° C. with either non-targeted or $\alpha_v\beta_3$-targeted melittin-carrying nanoparticles and washed in cold phosphate buffered saline (PBS). The washed cells were centrifuged and resuspended in the annexin-binding buffer (700 mM NaCl, 12.5 mM $CaCl_2$ in 15 mL of 50 mM Hepes, pH 7.4). FITC-Annexin V (5 µl) and 7-AAD (5 µl) were then added to each 100 µl of cell suspension. The cells were further incubated at room temperature for 15 min at the end of which 400 µl of 1× annexin-binding buffer was mixed and the samples kept on ice until analyzed by flow cytometry. The cells were analyzed on an Epics XL-MCL flow cytometer using the System II version 3.0 software (Beckman Coulter, Inc., Miami, Fla.) with the laser excitation wavelength at 488 nm. The green signal from FITC-annexin V was measured at 525 nm and the red signal from 7-AAD was measured at 620 nm. The minimal spectral overlap between FITC and 7-AAD allowed optimal signal separation.

The cells were categorized in four groups: Group 1: viable cells (FITC −, 7-AAD −); Group 2: early apoptosis (FITC +, 7-AAD −); Group 3: late apoptosis (FITC +, 7-AAD +) and Group 4: necrosis (FITC −, 7-AAD +), and the results are shown in Table 1.

TABLE 1

| Melittin nanoparticles ($\times 10^{-6}$ M) | Viable % | Early apoptosis % | Late apoptosis % | Necrosis % |
| --- | --- | --- | --- | --- |
| 10 | 15.03 ± 1.02 | 83.51 ± 2.58 | 1.44 ± 0.08 | 0.02 ± 0.01 |
| 20 | 4.97 ± 0.17 | 90.33 ± 3.1 | 4.67 ± 1.14 | 0.03 ± 0.01 |
| 25 | 1.57 ± 0.09 | 92.35 ± 2.97 | 6.06 ± 1.1 | 0.02 ± 0.02 |

A dose-dependent decrease was observed in the percentage of viable cells after 1 hr incubation with $\alpha_v\beta_3$-targeted melittin-loaded nanoparticles. Concurrently, there was a dose-dependent increase in the percent of early apoptotic and late-apoptotic cells. No necrosis was observed up to a concentration of 25 µM melittin, two times the $IC_{50}$ for cell death.

Intracellular Trafficking of Melittin

To track the melittin being delivered to the cells and define its localization, fluorescently labeled melittin was created. FluoroTag™ FITC Conjugation kit (Sigma, St. Louis, Mo.) was used to conjugate FITC to the N-terminus of melittin. Briefly, fluorescein-isothiocyanate and melittin were mixed in a 0.1 M carbonate-bicarbonate buffer (pH 9.0) in molar ratios of 10:1. After overnight incubation at room temperature with constant stirring, the reaction mixture was passed through a G-25 sephadex column and the fractions were collected and pooled. The column was regenerated by washing with PBS to remove the unbound FITC. The fractions with $A_{280}>0.4$ were pooled together and the conjugation ratio estimated by using $$\text{Molar } FITC/\text{protein} = \frac{A_{495} \times C}{A_{280} - [(0.35 \times A_{495})]}$$

$$\text{where } C = \frac{MW \times E_{280}}{389 \times 195}$$

MW is the molecular weight of the protein
389 is the molecular weight of FITC
198 is the absorption $E_{280}$ of bound FITC at 490 nm at pH 13.0
$(0.35 \times A_{495})$ is the correction factor due to absorbance of FITC at 280 nm
$E_{280}$ is the absorption at 280 nm of a protein at 1.0 mg/mL.

Perfluorocarbon nanoparticles carrying fluorescein-melittin and targeted by peptidomimetic vitronectin antagonist to the $\alpha_v\beta_3$-integrin receptor were incubated with C-32 melanoma cells for 1 hr at 37° C. After removing the unbound particles with PBS washing, the cells were fixed with 4% paraformaldehyde for 10 min at room temperature and visualized using a Zeiss 510 confocal microscope. Confocal Z-stack images were obtained to confirm the intracellular deposition of FITC-melittin. To further delineate the mechanism of cell entry, the temperature dependence and energy dependence of the internalization was assessed by repeating the experiment at 4° C. and after ATP depletion that was achieved by treating the cells with 20 mM sodium azide and 50 mM 2-deoxyglucose for 15 min at 37° C. prior to addition of the targeted FITC-melittin nanoparticles.

Figure 8:
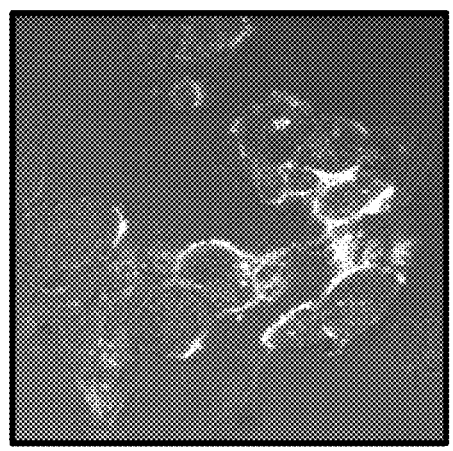
FIG. 8 shows the intracellular distribution of fluorescein labeled melittin in C-32 melanoma cells visualized by confocal microscopy.
Figure 8:
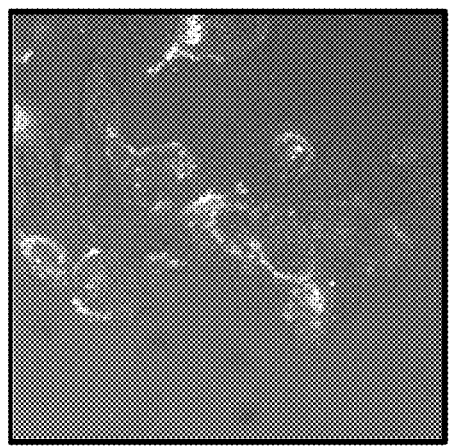
Figure 8:
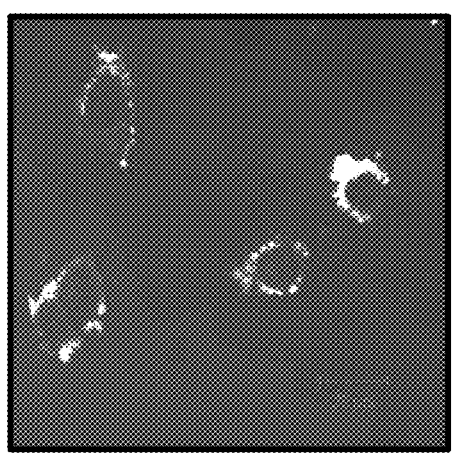
Figure 8:
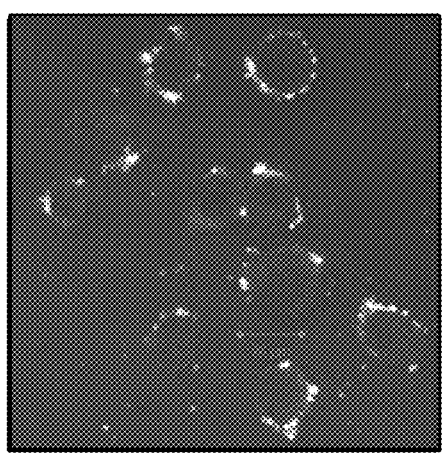

Confocal micrographs of C-32 melanoma cells illustrate internalization of FITC-melittin delivered from $\alpha_v\beta_3$-targeted melittin-loaded nanoparticles as shown in FIGS. 8A-8D where scale bars are 20 μM. After incubation at 37° C. for 1 hour, uniform cell membrane fluorescence is observed along with some diffuse intracellular fluorescence (FIGS. 8A and 8B). The absence of punctate intracellular fluorescence at 37° C. suggests that particle endocytosis is not the dominant mechanism of melittin internalization, as we have observed under other conditions with transport of compounds into cells. The inhibition of FITC-melittin internalization by cooling to 4° C. (FIG. 8D) or by ATP depletion (FIG. 8C), as confirmed by the absence of intracellular fluorescence, suggests that the melittin enters the cells through an energy-dependent process. Thus the mechanism of cellular melittin internalization when delivered by perfluorocarbon nanoparticles is cell membrane endocytosis.

Effect of Cholesterol Depletion

The role of cholesterol in modulating the melittin activity on the cell membrane was assessed by depleting cells of cholesterol before the cell proliferation assay and flow cytometry (as described above). C-32 Melanoma cells were treated with either 0.25 mM or 0.5 mM methyl beta cyclodextrin (Sigma, St. Louis, Mo.) for 15 min at 37° C. to deplete cholesterol. To quantify the amount of cholesterol depleted by methyl beta cyclodextrin, total lipids were extracted from melanoma cells by standard procedure. Briefly, $10^6$ C-32 melanoma cells grown in 6-well tissue culture plates were scraped by a rubber policeman and the pellet obtained post-centrifugation was treated with 200 μl chloroform-methanol (2:1). After spinning top speed in a microcentrifuge, the organic phase was collected and vacuum dried. The dried lipids were then dissolved in 20 μl of 2-propanol containing 10% triton-X 100 as assay samples. The total cholesterol content in the cells was determined by using the Amplex® Red Cholesterol Assay kit (Sigma, St. Louis, Mo.). Cholesterol standard was used for calibration as per manufacturer's recommendations.

The effect of cholesterol depletion on cell death was studied by both the MTT assay and annexin V-FITC/7-AAD staining by flow-cytometry. At low concentrations, methyl beta cyclodextrin (0.25 mM and 0.5 mM) cause a 7% and 12% depletion of cholesterol respectively, but no change in cell proliferation. When such cholesterol-depleted cells were treated with $\alpha_v\beta_3$-targeted melittin nanoparticles, a significant difference ($p<0.05$) was found in the cell viability of normal and cholesterol depleted cells for both the concentrations of melittin-nanoparticles (5 and 10 μM). The dramatic reduction in cell proliferation after 12% cholesterol depletion and treatment with melittin-nanoparticles (100% cell death for both 5 and 10 μM melittin-nanoparticles) was analyzed with flow cytometry of annexin-V FITC and 7-AAD staining. Under these conditions, cell debris was evident consistent with necrotic cell death in this case.

Cytochrome c Release Assay

Cytochrome c is a water-soluble 15 kDa protein residing in the mitochondrial intermembrane space and is released early during apoptosis. To determine if melittin-loaded nanodroplets trigger release of cytochrome c, C-32 melanoma cells were treated with varying concentrations of melittin-nanoparticles for 1 hour at 37° C. following which the mitochondria were isolated by using the Mitochondrial Isolation Kit (Pierce Biotechnology, Rockford, Ill.). The cytochrome c present in the mitochondrial and cytosol fractions thus obtained was assayed by using the cytochrome c ELISA kit (Invitrogen, Carlsbad, Calif.).

The cytochrome c release assay indicates that both free melittin and $\alpha_v\beta_3$-targeted melittin-nanoparticles cause a dose-dependent release of cytochrome c from the mitochondria of melanoma cells.

Lactate Dehydrogenase Release Assay

Lactate dehydrogenase (LDH) is a stable enzyme that is rapidly released from the cells upon plasma membrane damage. The lactate dehydrogenase release assay kit was obtained from BioVision (Mountain View, Calif.) and the assay performed according to manufacturers instructions. Briefly, C-32 melanoma cells were either treated with free melittin or melittin-nanoparticles at various concentrations for 1 hour at 37° C. and the amount of lactate dehydrogenase released quantified. Cells treated with 0.1% triton-X 100 were taken as 100% release.

There was no significant difference in LDH release from control cells and cells treated with melittin-loaded nanoparticles indicating that cell membrane integrity was maintained. However, free melittin caused a dose-dependent increase in LDH release. At a concentration of 1 μM, 19.17 (±4.2) percent LDH release was observed while 68.14 (±7.1) percent release was observed at 5 μM. Taken together, the LDH release and cytochrome c release data therefore suggest that free melittin at the lower concentration causes release of both LDH and cytochrome c, but at the higher concentrations causes a greater release of LDH (68.14±4.3%) than cytochrome c (55.48±6.1%). For $\alpha_v\beta_3$-targeted melittin-nanoparticles, there was a dose dependent increase in cytochrome c release, but no LDH release up to a concentration of 25 μM.

Example 5

Effect of Melittin Nanoparticles in Tumor Models

B16 Melanoma

In this model, one million B16F10 melanoma cells were implanted in the right flank of C57BL/6 mice on day 0. Three groups of mice in each group were employed. The control group was provided saline. A second group with non-targeted melittin nanoparticles prepared as described in Example 1 except that the $\alpha_v\beta_3$ targeting ligand was not included in the lipid/surfactant layer. In group 3, $\alpha_v\beta_3$ targeted melittin nanoparticles prepared as in Example 1 were employed.

The animals were dosed on days 4, 6, 8 and 10 through the tail vein. The dose in groups 2 and 3 was at 8 mg/kg of melittin contained in 3 ml emulsion administered per kg.

The mice were imaged with ultrasound and sacrificed on day 13. End tumor volumes and end tumor weights were measured.

Figure 9A:
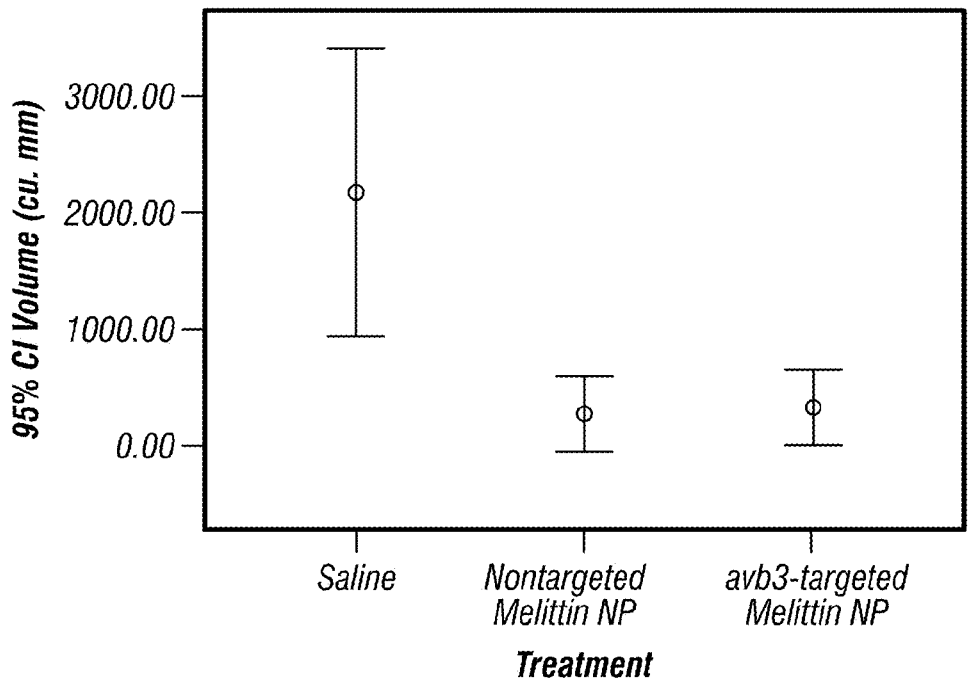
FIGS. 9A and 9B show the effect of both targeted and non-targeted nanoparticles containing melittin on tumor weight and volume in an in vivo tumor model.
Figure 9B:
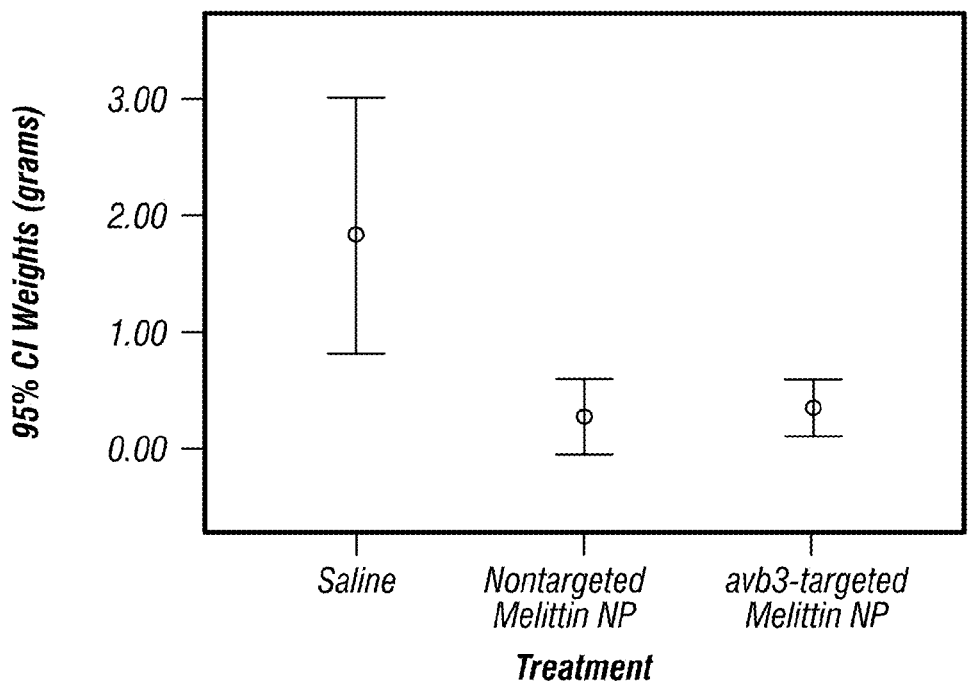

The results are shown in FIGS. 9A and 9B. As shown in FIG. 9A, the end volumes in cubic millimeters ($mm^3$) were as follows:

Control group, saline: 2,170 (±995);
Nontargeted melittin nanoparticles: 285 (±207); and
$\alpha_v\beta_3$-targeted melittin nanoparticles: 337 (±198).

Similarly, the end tumor weights in grams as shown in FIG. 9B were as follows:

Saline: 1.90 (±0.88);
Nontargeted melittin nanoparticles: 0.28 (±0.18);
$\alpha_v\beta_3$ targeted melittin nanoparticles: 0.33 (±0.16).

As shown, significant tumor shrinkage was obtained with either targeted or nontargeted melittin contained in nanoparticles.

It appeared that administration of saline diminished the level of hemoglobin. Neither the targeted nor nontargeted melittin nanoparticles had this effect. There were no significant differences between body weights obtained in the three groups.

The effect of the various treatments on blood components is shown in Table 2 below.

TABLE 2

| Test | Saline | Nontargeted Melittin NPs | $\alpha_v\beta_3$-targeted Melittin NPs |
| --- | --- | --- | --- |
| ALT (U/L) | 71.8 ± 21.89 | 73.0 ± 8.9 | 59.00 ± 10.1 |
| AST (U/L) | 2097.4 ± 1162.7 | 329.4 ± 263.39 *** | 306.8 ± 162.2 *** |
| ALKP (U/L) | 58.4 ± 27.7 | 94.4 ± 20.76 * | 119.2 ± 11.82 ** |
| Bilirubin (mg/dL) | <0.1 | <0.1 | <0.1 |
| Albumin (gm/dL) | 1.82 ± 0.04 | 1.8 ± 0.14 | 1.82 ± 0.17 |
| BUN (mg/dL) | 18.0 ± 2.6 | 20.4 ± 1.81 | 20.6 ± 2.07 |
| Creatinine (mg/dL) | 0.4 | 0.4 | 0.4 |
| Amylase (U/L) | 2435 ± 913 | 2157 ± 479 | 2064 ± 167 |

AST
*** p = 0.004
ALKP
* p = 0.048;
** p = 0.002
Aspartate aminotransferase (AST) is increased in saline treated control mice due to liver metastases.

Example 6

In Vivo Effect on MDA-435 Xenografts

Figure 10:
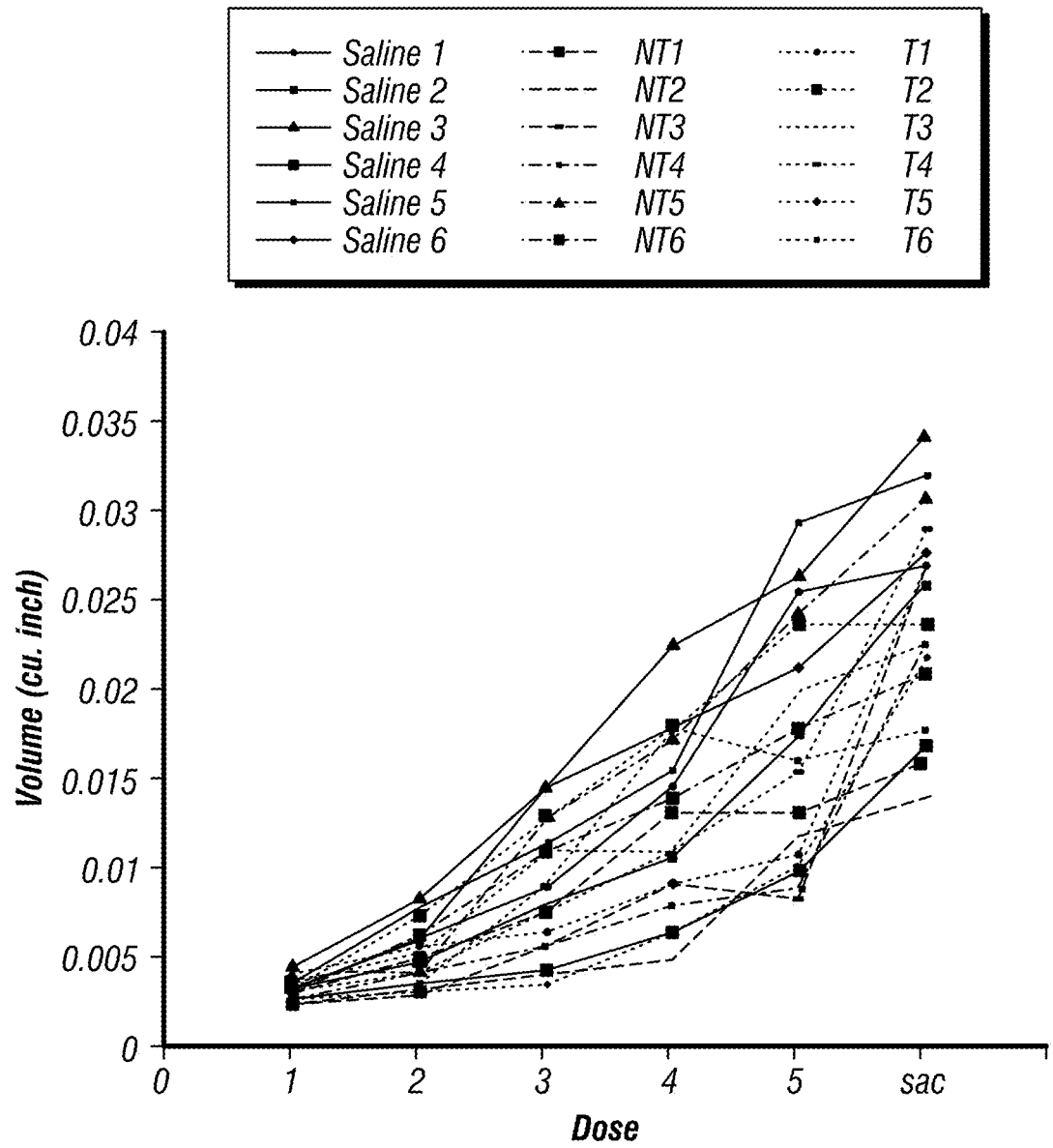
FIG. 10 shows the effect of targeted and non-targeted melittin-containing nanoparticles on tumor volume in individual murine tumor models.

Mice containing xenografts were prepared using two million MDA-435 cells in 50 µl; 50 µl of matrigel, 100 ng/ml of VEGF, 100 ng/ml of bFGF inserted into the linguinal fat pad on day 0. Again, three groups of mice were administered either saline or targeted or nontargeted melittin containing nanoparticles on days 7, 10, 13, 16, 19 and 22. The dose level was 5 mg/kg melittin for groups 2 and 3. The mice were sacrificed and tumor volume was determined. Group 3 showed a 24.68% reduction in tumor growth rate as compared to the control and the targeted nanoparticles an 11.18% reduction. However, the results among groups were scattered as shown in FIG. 10.

The invention claimed is:

1. A method to prepare a composition comprising nanoparticles, which nanoparticles comprise a liquid hydrophobic core coated with a lipid/surfactant layer, wherein said lipid/surfactant layer contains at least one membrane-integrating peptide and optionally a targeting ligand, which method comprises incubating nanoparticles comprising a hydrophobic core coated with a lipid/surfactant layer, optionally containing a targeting ligand, with at least one membrane-integrating peptide, wherein the membrane-integrating peptide comprises a hydrophobic amino acid sequence of 10-30 amino acids adjacent to a cationic amino acid sequence of 3-6 amino acids, and is a membrane lytic or membrane pore-forming peptide.

2. The method of claim 1, wherein the membrane-integrating peptide is melittin.

3. The method of claim 1, wherein said lipid/surfactant layer contains a targeting ligand.

4. The method of claim 1, wherein the hydrophobic core comprises at least one halocarbon compound.

5. The method of claim 4, wherein the halocarbon compound is a perfluorocarbon.

6. The method of claim 1, wherein the lipid/surfactant layer comprises at least one phospholipid.

7. The method of claim 1, wherein the membrane-integrating peptide is cytotoxic.

8. The method of claim 3, wherein the targeting ligand specifically binds an integrin.

9. The method of claim 1, wherein said lipid/surfactant layer further includes a therapeutic or diagnostic agent.

10. The method of claim 1, wherein the membrane-integrating peptide is covalently linked to a therapeutic or diagnostic agent.

* * * * *